US009492098B2

(12) United States Patent
Davis et al.

(10) Patent No.: US 9,492,098 B2
(45) Date of Patent: Nov. 15, 2016

(54) VISUAL ELECTROPHYSIOLOGY DEVICE

(71) Applicant: LKC Technologies, Inc., Gaithersburg, MD (US)

(72) Inventors: Charles Quentin Davis, Frederick, MD (US); Frank Hunleth, Rockville, MD (US)

(73) Assignee: LKC TECHNOLOGIES, INC., Gaithersburg, MD (US)

( * ) Notice: Subject to any disclaimer, the term of this patent is extended or adjusted under 35 U.S.C. 154(b) by 0 days.

(21) Appl. No.: 14/763,275

(22) PCT Filed: Jan. 28, 2014

(86) PCT No.: PCT/US2014/013395
§ 371 (c)(1),
(2) Date: Jul. 24, 2015

(87) PCT Pub. No.: WO2014/117154
PCT Pub. Date: Jul. 31, 2014

(65) Prior Publication Data
US 2015/0342495 A1    Dec. 3, 2015

Related U.S. Application Data

(60) Provisional application No. 61/842,102, filed on Jul. 2, 2013, provisional application No. 61/836,971, filed on
(Continued)

(51) Int. Cl.
*A61B 3/14* (2006.01)
*A61B 3/10* (2006.01)
(Continued)

(52) U.S. Cl.
CPC ........... *A61B 5/0496* (2013.01); *A61B 3/0008* (2013.01); *A61B 3/112* (2013.01); *A61B 3/12* (2013.01);
(Continued)

(58) Field of Classification Search
USPC ........................................ 351/206, 221, 246
See application file for complete search history.

(56) References Cited

U.S. PATENT DOCUMENTS

| 4,523,820 A | 6/1985 | Kaakinen |
|---|---|---|
| 5,382,987 A | 1/1995 | Sperling |

(Continued)

OTHER PUBLICATIONS

International Search Report Issued in International PCT Application PCT/US2014/013395 dated Jun. 17, 2014.
(Continued)

*Primary Examiner* — Jack Dinh
(74) *Attorney, Agent, or Firm* — Sean Wooden; Andrews Kurth Kenyon LLP

(57) ABSTRACT

To assess visual system function, a device monitors electrical response to a visual stimulus. Stimulus generation includes controlling the timing of component flashes comprising the visual stimulus and modulating the timing between the visual stimulus and other device operations, including image acquisition and infrared flashes. Other stimulus generation includes controlling retinal illumination for sinusoidal, triangular, and square stimuli as well as nonlinear adjustments of stimulus luminance as a function of pupil area. Ease of use improvements includes operation with electrode arrays. Error condition monitoring includes determining the presence of: an eye's pupil; impedance between electrodes that monitor the electrical response; and undesirable levels of external light.

20 Claims, 6 Drawing Sheets

Related U.S. Application Data

Jun. 19, 2013, provisional application No. 61/757,316, filed on Jan. 28, 2013.

(51) Int. Cl.
| | | |
|---|---|---|
| *A61B 3/00* | (2006.01) | |
| *A61B 5/0496* | (2006.01) | |
| *A61B 3/12* | (2006.01) | |
| *A61B 3/11* | (2006.01) | |
| *A61B 5/053* | (2006.01) | |

(52) U.S. Cl.
CPC ................ *A61B 3/14* (2013.01); *A61B 5/053* (2013.01); *A61B 2562/0257* (2013.01); *A61B 2562/043* (2013.01)

(56) References Cited

U.S. PATENT DOCUMENTS

| | | |
|---|---|---|
| 5,943,116 A | 8/1999 | Zeimer |
| 6,247,813 B1 | 6/2001 | Kim et al. |
| 6,616,277 B1 | 9/2003 | Davenport |
| 2008/0058655 A1 | 3/2008 | Severns |
| 2009/0109399 A1 | 4/2009 | Severns |
| 2009/0201467 A1 | 8/2009 | Smith |
| 2010/0060728 A1 | 3/2010 | Bublitz et al. |
| 2011/0040202 A1 | 2/2011 | Luo et al. |
| 2012/0182523 A1 | 7/2012 | Wyatt |

OTHER PUBLICATIONS

Alpern, M, et al. "The Dependence of the Photopupil Response on Flash Duration and Intensity" The Journal of General Physiology, vol. 42, No. 2, pp. 265-278 (1963).

VISUAL ELECTROPHYSIOLOGY DEVICE

RELATED APPLICATIONS

This application is a national stage application under 35 U.S.C. §571 based on PCT Application No. PCT/US2014/013395, entitled "Visual Electrophyphysiology Device" and filed Jan. 28, 2014, which claims the benefit of U.S. Provisional Application Ser. No. 61/842,102, entitled "VISUAL ELECTROPHYSIOLOGY DEVICE" and filed Jul. 2, 2013. The entirety of the aforementioned applications are incorporated herein by reference.

GOVERNMENT RIGHTS

Inventions described herein were made with government support under grant 9R44EY021121 awarded by the National Institutes of Health, USA. Accordingly, per the terms and conditions of the grant, the U.S. government has certain rights in the present application.

FIELD

The embodiments described herein relate to improved devices and methods for assessing visual system function.

BACKGROUND

The electroretinogram (ERG) and visual evoked potentials (VEP) are diagnostic tests used to help assess visual system function. See, for example, the textbook *Principles and Practice of Clinical Electrophysiology of Vision*, $2^{th}$ edition, edited by Heckenlively and Arden (2006), which describes dozens of diseases that can be diagnosed with the aid of visual electrophysiology. Standards have been developed for the most common of these tests, as described in Marmor et al. (2009), Hood et al. (2012), Holder et al. (2007), and Odom et al. (2010). As a specific example, some features of the clinical ERG are strongly correlated with diabetic retinopathy (Bresnick and Palta (1987), Han and Ohn (2000) and Satoh et al. (1994)). As another example, Kjeka et al. (2013) showed greatly improved outcomes for the treatment of central retinal vein occlusion when basing treatment decisions on ERG results rather than ophthalmologic examinations alone.

Normally, ERG measurements are recorded using a large instrument (e.g., the LKC Technologies UTAS system) in a darkened room with electrodes placed directly onto the eye. Dilating drops are used to enlarge the pupil and anesthetic drops are used to numb the eye before placing the electrodes onto the eye. The eye is stimulated with light to elicit a response from the visual system which is recorded via the electrodes. The measurements are performed by a skilled technician, and the results are usually interpreted by an ophthalmologist or PhD expert in visual electrophysiology. The invasiveness and complexity described above have prevented the ERG from having widespread use in assessing diabetic retinopathy and other diseases.

The invention described in U.S. Pat. No. 7,540,613 helps prevent these disadvantages. Nevertheless, there still exists a need for visual electrophysiology devices that are easier to use and/or have improved performance.

SUMMARY

Described herein are embodiments of a device and method for providing an indication of visual system function. The improvements disclosed herein can be used separately or in combination, including improvements in stimulus generation, ease of use, and error condition monitoring. Embodiments overcome the problems described above.

An embodiment of a device to provide an indication of visual system function of a patient has a first light emitter having a first emission spectrum. The device also has an optical assembly arranged so that light emitted from the first light emitter reaches an eye of the patient. The device also has a camera arranged to image the eye of the patient and a controller. The controller modulates a light emission from the first light emitter to create a light stimulus that receives and analyzes an electrical signal from the visual system of the patient and that provides an indication of visual system function based on that analysis.

In some embodiments, the device further includes a second light emitter having a visible second emission spectrum that is distinct from the first emission spectrum, wherein the optical assembly is arranged so that light emitted from the second light emitter reaches an eye of the patient. In this case, the controller measures the eye's pupil area using images from the camera and adjusts the luminance of the light stimulus as a function of the eye's pupil area and wherein the controller modulates light emission from the first and second light emitters to create first and second flashes overlapping in time.

In another embodiment, the light stimulus comprises one or more flashes of light and the controller synchronizes the camera and the light stimulus so that the camera is only activated when there is no flash.

In another embodiment, the controller measures the eye's pupil area using images received from the camera and adjusts the luminance in the light stimulus through a non-linear, concave function of the eye's pupil area.

In another embodiment, the controller does not provide an indication of visual system function unless the eye's pupil has been identified.

In another embodiment, the device further includes a light detector adapted to measure light emitted from the first light emitter, wherein the controller does not provide an indication of visual system function if the signal from the light detector differs from a set of expected light detector signals that includes excessive external light.

In another embodiment, the controller measures the eye's pupil area using images from the camera and adjusts the luminance of the light stimulus as a function of the eye's pupil area. In addition, the device further includes an electrical impedance meter, wherein the controller does not provide an indication of visual system function unless the electrical impedance meter measures an impedance smaller than a target value.

In another embodiment, the controller modulates a light emission from the first light emitter so as to deliver to the eye a periodic visual stimulus that approximates a retinal illuminance that varies as one of a sinusoid, a square wave having a duty cycle between 30% and 70%, or a triangular wave.

In some embodiments, the controller modulates a light emission from the first light emitter to create a first flash of light having a duration less than 21 ms. The controller also modulates a light emission from the second light emitter to create a second flash of light having a duration less than 21 ms. The first and second flashes may overlap in time by at least 50% of the longer of the two flashes. The controller may receive images from the camera and uses those images to measure the eye's pupil area and adjusts the energy in the first flash as a function of the area. The controller can further receive and analyze an electrical signal from the visual system of the patient so as to provide an indication of visual system function.

In accordance with another embodiment, a device to provide an indication of visual system function of a patient has a first light emitter having a first emission spectrum that has at least 50% of its energy emitted between 400 nm and 710 nm. The device also has a camera arranged to image an eye of the patient. The device also has an optical assembly arranged so that light emitted from the first light emitter reaches the eye. The device also has a controller that modulates a light emission from the first light emitter to create a first flash of light having a flash frequency greater than 1 Hz. The controller receives images from the camera at a frame rate. The controller measures the eye's pupil area using the images and adjusts the energy in the first flash as a function of the area. The ratio of the flash frequency to the frame rate is an integer or one over an integer. The controller can further receive and analyze an electrical signal to provide an indication of visual system function.

In accordance with another embodiment, a device to provide an indication of visual system function of a patient has a first light emitter having a first emission spectrum that has at least 50% of its energy emitted between 400 nm and 710 nm. The device also has an infrared light emitter having a second emission spectrum that has at least 50% of its energy emitted at wavelengths longer than 710 nm. The device also has an optical assembly arranged so that light emitted from the first light emitter and the infrared light emitter reaches an eye of the patient. The device also has a controller. The controller modulates a light emission from the first light emitter to create a first flash of light having a duration less than 21 ms. The controller also modulates a light emission from the infrared light emitter to create an infrared flash of light having a duration less than 40 ms. The energy emitted by the first light emitter during the infrared flash of light is less than 50% of the energy emitted by infrared light emitter during the infrared flash of light. The controller can further receive and analyze an electrical signal from the visual system of the patient so as to provide an indication of visual system function.

In accordance with another embodiment, a device to provide an indication of visual system function of a patient includes an electrode array comprising three electrodes structurally adapted to be applied and removed from the skin as a single unit. The device also has an analog to digital converter that measures the electric potential difference between a first electrode and a second electrode in the electrode array. The device also has a common-mode attenuation circuit electrically connected to a third electrode in the electrode array. The distance between the first and second electrode is greater than the distance between the first electrode and third electrode and the distance between the first and second electrode is greater than the distance between the second electrode and third electrode. The device also has a controller.

In certain embodiments, the device has a first light emitter having a first emission spectrum that has at least 50% of its energy emitted between 400 nm and 710 nm and an optical assembly arranged so that light emitted from the first light emitter reaches an eye of the patient. The controller may modulate a light emission from the first light emitter to create a first flash of light having a duration less than 21 ms. The controller can further receive and analyze the electrical signal to provide an indication of visual system function based on that analysis.

In accordance with another embodiment, a device to provide an indication of visual system function of a patient has a first light emitter having a first emission spectrum that has at least 50% of its energy emitted between 400 nm and 710 nm. The device also has an optical assembly arranged so that light emitted from the first light emitter reaches an eye of the patient. The device also has a camera arranged to image the eye of the patient. The device also has a controller that modulates a light emission from the first light emitter to create a first flash of light having a duration less than 21 ms. The controller also receives images from the camera and can further receive and analyze an electrical signal from the visual system of the patient so as to provide an indication of visual system function. The controller does not provide the indication until after the eye's pupil has been identified.

In accordance with another embodiment, a device to provide an indication of visual system function of a patient has an electrode that receives an electrical signal from the visual system of the patient. The device also has a first light emitter having a first emission spectrum that has at least 50% of its energy emitted between 400 nm and 710 nm. The device also has an optical assembly arranged so that light emitted from the first light emitter reaches the eye. The device also has a light detector that measures light emitted from the first light emitter. The device also has a controller. The controller modulates a light emission from the first light emitter to create a first flash of light and can further receive and analyze the electrical signal to provide an indication of visual system function. The controller can also receive a signal from the light detector, and the controller does not provide the indication if the signal from the light detector differs from a set of expected light detector signals.

In accordance with another embodiment, a device to provide an indication of visual system function of a patient has a first light emitter having a first emission spectrum that has at least 50% of its energy emitted between 400 nm and 710 nm. The device also has an optical assembly arranged so that light emitted from the first light emitter reaches the eye. The device also has a light detector that measures light emitted from the first light emitter. The device also has a controller. The controller modulates a light emission from the first light emitter to create a first flash of light and can further receive and analyze an electrical signal from the visual system of the patient to provide an indication of visual system function. The controller can also receive a signal from the light detector, whereby the controller does not provide the indication if the signal from the light detector differs from a set of expected light detector signals.

In accordance with another embodiment, a device to provide an indication of visual system function of a patient has a first light emitter having a first emission spectrum that has at least 50% of its energy emitted between 400 nm and 710 nm. The device also has an optical assembly arranged so that light emitted from the first light emitter reaches an eye of the patient. The device also has a camera arranged to image the eye of the patient. The device also has a controller that modulates a light emission from the first light emitter to create a first flash of light having a duration less than 21 ms. The controller receives images from the camera, measures the eye's pupil area using images from the camera, and adjusts the energy in the first flash as a function of the area. The controller can also receive and analyze an electrical signal from the visual system of the patient so as to provide an indication of visual system function. The device also has an electrical impedance meter and the controller does not provide the indication until after the electrical impedance meter measures an impedance smaller than 1 GΩ.

In accordance with another embodiment, a method for providing an indication of visual system function of a patient includes illuminating an eye of the patient with a first flash of visible light having a duration of less than 21 ms and having a first emission spectrum. The method additionally includes illuminating the eye of the patient with a second flash of visible light having a duration of less than 21 ms and having a second emission spectrum distinct from the first emission spectrum. The first flash and second flash overlap in time by at least 50% of the longer of the two flashes. The method further includes measuring the eye's pupil area, adjusting the energy in the first flash as a function of the eye's pupil area and receiving and analyzing an electrical signal from the patient and providing an indication of visual system function based on that analysis. The method may further involve imaging the eye of the patient, receiving images from the camera, measuring the eye's pupil area using images from the camera, and adjusting the energy in the first flash as a function of the area.

In accordance with another embodiment, a method for providing an indication of visual system function of a patient includes the step illuminating an eye of the patient with a visible light stimulus comprising flashes of light having a flash frequency greater than 7 Hz. The method further includes measuring the eye's pupil area at a frame rate frequency, adjusting the luminance of the visible light stimulus as a function of the eye's pupil area, and receiving and analyzing an electrical signal from the patient and providing an indication of visual system function based on that analysis, wherein the ratio of the flash frequency to the frame rate frequency is within 1% of an integer or within 1% of the reciprocal of an integer.

The method may further involve illuminating the eye of the patient with infrared flashes of light that have at least 50% of their energy emitted at wavelengths longer than 710 nm and an infrared flash frequency greater than 1 Hz, wherein the energy in the first visible light stimulus emitted during the infrared flashes is less than 50% of the infrared energy emitted during the infrared flashes. The method may further involve measuring the eye's pupil area at a frame rate frequency, adjusting the luminance of the first visible light stimulus as a function of the eye's pupil area and illuminating the eye of the patient with a second visible light stimulus. In this case, the first visible light stimulus may include a first flash of visible light having a duration of less than 21 ms and a first emission spectrum. The second visible light stimulus may include a second flash of visible light having a duration of less than 21 ms and a second emission spectrum distinct from the first emission spectrum. Further, the first and second flashes of visible light may overlap in time by at least 50% of the longer of the two flashes of visible light, whereby the ratio of the infrared flash frequency to the frame rate frequency is within 1% of an integer or within 1% of the reciprocal of an integer.

In accordance with another embodiment, a method for providing an indication of visual system function of a patient involves placing an electrode array comprising three electrodes on the skin of the patient as a single unit, wherein the three electrodes include a first electrode, a second electrode and a third electrode, whereby the first and second electrode are more distant from each other than any other pairing of the first, second, and third electrodes and whereby the third electrode is electrically connected to a common-mode attenuation circuit. The method further includes the step of illuminating an eye of the patient with a first visible light stimulus, measuring the electric potential difference between the first electrode and the second electrode, and providing an indication of visual system function based on that measurement.

The method may further include the step of illuminating the eye of the patient with infrared flashes of light having at least 50% of their energy emitted at wavelengths longer than 710 nm and having an infrared flash frequency greater than 1 Hz, measuring the eye's pupil area at a frame rate frequency, and adjusting the luminance of the light stimulus as a function of the eye's pupil area, wherein the ratio of the flash frequency to the frame rate frequency is within 1% of an integer or within 1% of the reciprocal of an integer. The method may further includes the step of illuminating the eye of the patient with a second visible light stimulus. In this case, the first visible light stimulus may have a stimulus frequency greater than 7 Hz, including a first flash of visible light having a duration of less than 21 ms and having a first emission spectrum. The second visible light stimulus may include a second flash of visible light having a duration of less than 21 ms and a second emission spectrum distinct from the first emission spectrum. The energy in the first flash of visible light emitted during the infrared flashes may be less than 50% of the infrared energy emitted during the infrared flashes, and the first and second flashes of visible light may overlap in time by at least 50% of the longer of the two flashes, In accordance with another embodiment, a method for providing an indication of visual system function of a patient involves emitting a first light from a first light emitter, having a first emission spectrum that has at least 50% of its energy emitted between 400 nm and 710 nm, so that the first light reaches an eye of the patient. The method also involves emitting an infrared light from an infrared light emitter, having an infrared emission spectrum that has at least 50% of its energy emitted at wavelengths longer than 710 nm, so that the second light reaches an eye of the patient. The method also involves controlling the first light emitter to modulate a first light to create a first flash of light having a duration less than 21 ms. The method also involves controlling the infrared light emitter to modulate an infrared light to create an infrared flash of light having a duration less than 40 ms, wherein the energy emitted by the first light emitter during the infrared flash of light is less than 50% of the energy emitted by infrared light emitter during the infrared flash of light. Finally, the method involves receiving and analyzing an electrical signal from the patient so as to provide an indication of visual system function.

In accordance with another embodiment, a method for providing an indication of visual system function of a patient involves placing an electrode array comprising three electrodes on the skin as a single unit, wherein the three electrodes include a first electrode, a second electrode and a third electrode, a distance between the first and second electrode is greater than the distance between the first electrode and third electrode, and a distance between the first and second electrode is greater than the distance between the second electrode and third electrode. The method also involves emitting a first light from a first light emitter, having a first emission spectrum that has at least 50% of its energy emitted between 400 nm and 710 nm, so that the first light reaches an eye of the patient. The method also involves controlling the first light emitting to modulate a first light to create a first flash of light having a duration less than 21 ms. The method also involves measuring the electric potential difference between the first electrode and the second electrode so as to provide an indication of visual system function.

In accordance with another embodiment, a method for providing an indication of visual system function of a patient involves emitting a first light from a first light emitter, having a first emission spectrum that has at least 50% of its energy emitted between 400 nm and 710 nm, so that the first light reaches an eye of the patient. The method also involves controlling the first light emitting to modulate a first light to create a first flash of light having a duration less than 21 ms. The method also involves imaging the eye of the patient, receiving images from the camera, measuring the eye's pupil area using images from the camera and adjusting the energy in the first flash through a non-linear, concave function of the area. Finally, the method involves receiving and analyzing an electrical signal from the patient so as to provide an indication of visual system function.

In accordance with another embodiment, a method for providing an indication of visual system function involves emitting a first light from a first light emitter, having a first emission spectrum that has at least 50% of its energy emitted between 400 nm and 710 nm, so that the first light reaches an eye of the patient. The method also involves controlling the first light emitting to modulate a first light to create a first flash of light having a duration less than 21 ms. The method also involves imaging the eye of the patient, receiving images from the camera; and receiving and analyzing an electrical signal from the patient so as to provide an indication of visual system function, wherein the indication is not provided until the eye's pupil has been identified.

In accordance with another embodiment, a method for providing an indication of visual system function of a patient involves emitting a first light from a first light emitter, having a first emission spectrum that has at least 50% of its energy emitted between 400 nm and 710 nm, so that the first light reaches an eye of the patient. The method also involves controlling the first light emitting to modulate a first light to create a first flash of light having a duration less than 21 ms. The method also involves measuring the light emitted from the first light emitter with a light detector and receiving a signal from the light detector. Finally, the method involves receiving and analyzing an electrical signal from the patient so as to provide an indication of visual system function, wherein the indication is not provided if the signal from the light detector differs from a set of expected light detector signals.

In accordance with another embodiment, a method for providing an indication of visual system function of a patient involves emitting a first light from a first light emitter, having a first emission spectrum that has at least 50% of its energy emitted between 400 nm and 710 nm, so that the first light reaches an eye of the patient. The method also involves controlling the first light emitting to modulate a first light to create a first flash of light having a duration less than 21 ms. The method also involves imaging the eye of the patient and receiving images from the camera. The method also involves receiving and analyzing an electrical signal from the patient so as to provide an indication of visual system function. Finally, the method involves measuring an electrical impedance associated with the electrical signal received from the patient, wherein the indication is not provided until after the electrical impedance meter measures an impedance smaller than 1 GΩ.

BRIEF DESCRIPTION OF THE DRAWINGS

The accompanying drawings, which are incorporated in and constitute a part of this specification, illustrate several embodiments and together with the description, serve to explain the novel principles of the embodiments described herein. In the drawings:

FIG. 4 shows timing diagrams of light output versus time for exemplary embodiments described herein.

FIG. 5 shows timing diagrams of light output versus time for exemplary embodiments described herein.

DETAILED DESCRIPTION

Figure 1:
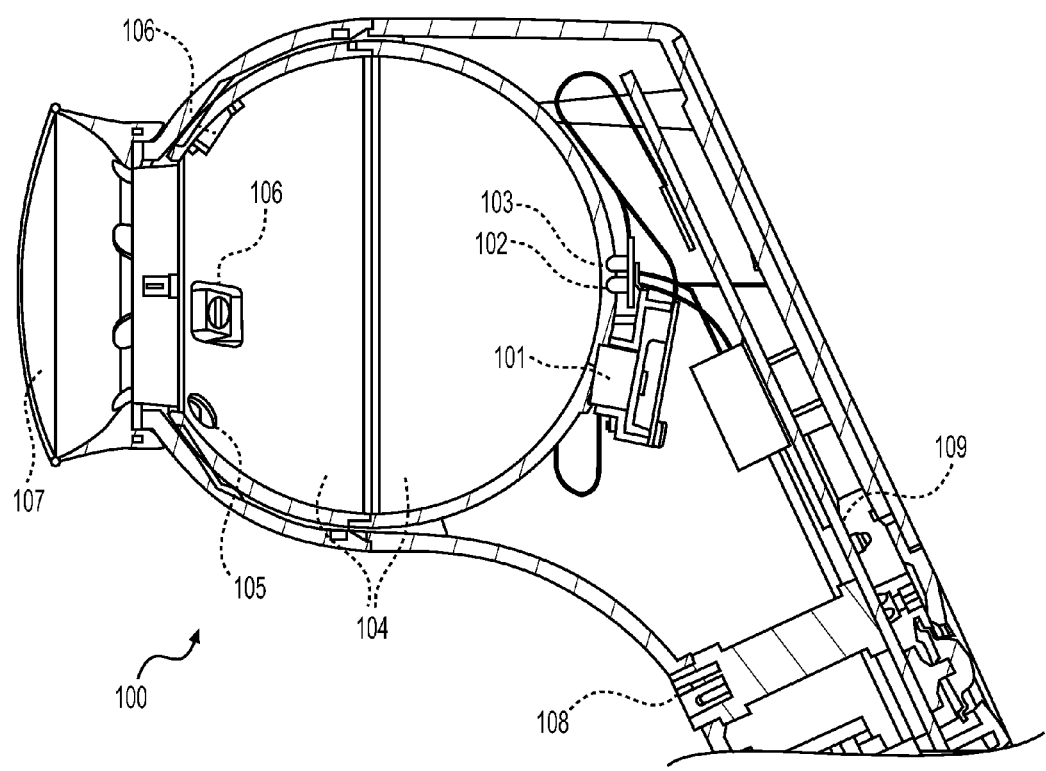
FIG. 1 is a cross sectional view of an exemplary visual electrophysiology device.

Disclosed herein are embodiments of improved visual electrophysiology devices and methods of improved visual electrophysiology. These devices and methods can be used to provide an indication of visual system function of a patient. There is an electrical circuit that controls a light stimulus directed toward the eye and measures the electrical signal the eye produces in response to the light. Device operation involves stimulating the eye with light and measuring an electrical response to the stimulus. By way of example, the time span between the flash of light and the time of the peak of the electrical response may be indicative of the degree of retinal ischemia in a patient.

Embodiments of the present invention may improve the measurements over existing visual electrophysiology device measurements, by making the stimulation more consistent, improving the data collection, and/or checking for error conditions. The stimulus to the eye can comprise flashes of light or other modulated light waveforms. The stimulus to the eye can comprise a single flash of light. The stimulus to the eye can comprise a background illumination that is perceptually constant or only slowly changing.

Embodiments may provide a first light emitter having a first emission spectrum. The first light emitter may have a first visible emission spectrum and may emit, for example, green, red, orange, blue, amber, or yellow light. The first light emitter may be a LED. Optionally, other (2, 3, 4, 5 or more) visible light emitters may be present with distinct spectra. For example, some embodiments may use 4 LEDs that each have red, green, and blue emitters. Some embodiments may have an infrared light emitter that emits at least 50% of its energy at wavelengths longer than 710 nm. Other light emitters may be provided.

Some embodiments may use a controller to modulate the emitters' output so that they emit light for periods of time (e.g., less than 6 ms, 21 ms or 40 ms) and so that the light emitted from at least some of the visible light emitters overlaps in time. In some embodiments, the emission duration for each emitter is different (e.g., the second light emitter emits light for a longer period of time than the first light emitter).

Some embodiments use a camera to measure the pupil size so the light stimulus luminance can be adjusted to reduce the effect of pupil size on the effective retinal stimulus; for example, the light stimulus luminance can be linearly related to the multiplicative inverse of the eye's pupil area or the light stimulus luminance can be related to the multiplicative inverse of the eye's pupil area through a non-linear, concave function.

The light emitters can be arranged to deliver retinal illuminances that are approximately sinusoidal, triangular, or square by for example continuously modulating the light output or by delivering flashes of light in a pulse-width modulation (PWM) fashion. In various embodiments, time or frequency synchronization between the light stimulus, optional infrared light flashes, and camera images may provide more consistent stimulation, image collection, light stimulus luminance adjustment, and the like. By varying the above-described characteristics of the light emitters as described herein, embodiments provide improved results over existing visual electrophysiology devices.

Embodiments may improve over existing visual electrophysiology devices by using electrode arrays and driving a middle electrode with a common-mode attenuation circuit while measuring electric potential differences between the more distantly separated outer electrodes. This electronic configuration maximizes the magnitude of the electric signals while providing the convenience of an easy to use electrode array.

Embodiments may improve over existing visual electrophysiology devices by checking for error conditions. Electrical impedance measurements may be used to confirm the device is electrically connected to the patient with a sufficiently low impedance. For example, it could determine if the electrode array does not stick sufficiently well to the patient to achieve an electrical connection. A light detector may be used for example to ensure undesired external light is sufficiently small and/or to ensure the desired light stimulus is in fact produced. Pupil detection may be used to ensure the patient's eye is present and open to ensure the light stimulus produced enters the patient's eye.

Combinations of the above description are also contemplated. Composition and methods of their use are contemplated. Embodiments improve over existing visual electrophysiology devices in other ways apparent from the detailed description herein.

DEFINITIONS

In order to more clearly understand the embodiments described herein, certain terms are defined as follows. Other terms are defined in other parts of this disclosure.

The term "light emitter" refers to anything that emits electromagnetic radiation in the UV, visible, and infrared (IR) range. Exemplary light emitters include LEDs, display devices, and gas-discharge devices such as xenon flash lamps and fluorescent bulbs. In some cases herein, the term "infrared" is abbreviated as "IR".

The term "LED" refers to a light emitting diode. LED includes those comprising semiconductor, organic, and quantum-dots. The term LED includes those with integrated phosphors.

The term "patient" refers a human or other mammal from which physiological electrical signals are to be measured. It is contemplated that the device will be placed in proximity to the patient to enable stimulation of the patient's visual system and measurement of physiological response thereto.

The term "retinal illuminance" refers to the product of luminance and pupil area. The unit Troland (abbreviated Td) is a measure of retinal illuminance where luminance has units of $cd/m^2$ and pupil area has units of $mm^2$.

The phrase "indication of visual system function" refers to the analysis of an electrical signal from the visual system of a patient in response to light. It is to be distinguished from other measures of the visual system based solely on e.g., imaging of the eye structure with fundus photography, OCT, or the like, or psychophysical measures such as visual acuity using a Snellen chart.

Description

Various embodiments, as well as additional objects, features, and advantages thereof, will be understood more fully from the following description.

FIG. 1 shows an exemplary device 100 used to provide an indication of visual system function of a patient. An eyecup 107 may contact the bony regions around the eye to keep the device against or near the patient. The light emitter 106 shines light into an optical assembly 104, which directs the light to the patient's eye. In this example, the optical assembly 104 acts as an integrating sphere to deliver the light emitted from the light emitter 106 in a diffuse manner to the patient's eye. A diffuse light source enables interrogation of large portion of the retina and makes patient fixation less important. Other exemplary optical assemblies do not require light from the light emitter 106 to be reflected before reaching the patient's eye, for example, the light may be refracted, diffused, scattered, or may have a direct path between the light emitter and the patient's eye.

The light emitter 106 can have 1, 2, 3, 4, or more emission sources. For example, the light emitter 106 can be a first light emitter, which may be a LED or different type of light emitter. The first light emitter has a first emission spectrum. In some embodiments, the first light emitter may emit green, red, orange, blue, amber, or yellow light. The first light emitter may be, for example, a green LED. The light emitter 106 can also be a second light emitter. The optional second light emitter has a visible second emission spectrum that, for example, is distinct from the first emission spectrum. The second light emitter, if present, may emit green, red, orange, blue, amber, or yellow light as long as the emission spectrum is distinct from the first emission spectrum. The optional second light emitter may be an LED or a different type of light emitter and may be, for example, a red LED. The light emitter 106 can also be a third light emitter. The optional third light emitter has a visible third emission spectrum that, for example, is distinct from the first and second emission spectra. The third light emitter, if present, may emit green, red, orange, blue, amber, or yellow light as long as the emission spectrum is distinct from the first and second emission spectra. The optional third light emitter may be an LED or a different type of light emitter, and may be, for example, a blue LED. The device 100 may have additional (e.g., 4, 5, 6, 7, 8, or more) visible light emitters having distinct spectra; for example, having 4 different visible spectral sources enables independent stimulation of one of the three types of cones or rods in a human (Shapiro et al. (1996)).

The light emitter 106 can be, for example, an RGB LED, for example, a CREE CLV6Aa, an Avago ASMT-MT000-0001, or an Osram LRTD-C9TP. The light emitter 106 can be, for example, a red, green, blue, white LED such as CREE XLamp XM-L. Individual LEDs or other light sources may be used. Two components in the light emitter 106 are visible in the cross section of the device 100; two more are on the other half, for a total of four. The number of components in the light emitter 106 need not be 4; 1, 2, 3, 4, 5, 6, 7, 8, 9, 10, 11, 12 or more is contemplated. A larger number of components comprising the light emitter 106 gives improved light uniformity in the integrating sphere and a brighter possible light output; however, larger numbers are inconvenient is terms of manufacturing difficulty and cost.

As shown in FIG. 1, a camera 101 can image the patient's eye through the hole in the optical assembly 104 and the eyecup 107. The eyecup 107 can be designed to rest on regions around a patient's eye so as to reduce the amount of light originating outside of the device 100 from reaching the eye. Alternatively, the eyecup 107 can be designed not to contact the patient. An optional fixation light 102 can provide a target for the patient to fixate on during the testing process. When using an infrared light emitter 103, at least 50% of its energy will be emitted at wavelengths longer than 710 nm. The infrared light emitter 103 can be used to illuminate the patient's eye during the exposure time of the camera 101. In some embodiments, the device 100 has neither a camera 101, nor an infrared light emitter 103.

Patient connector 108 can be used to make a set of electrical connections to the patient so as to be able to receive an electrical signal from the patient. The electrical signals can be gathered from the patient using any number of electrodes (e.g., 1, 2, 3, 4, 5, 6, 7, 8, 9, 10, or more) operationally connected to the device 100 via a cable. Exemplary locations to measure the response include on the surface of the eye (e.g., with electrodes such as Burian Allen electrodes, DTL electrodes, and ERG Jet electrodes), under the epithelium (e.g., with a needle electrode), on the skin near the eye (e.g., with LKC Sensor Strip electrodes as described in U.S. Patent application 61/696,499), on the back or top of the head (e.g., using gold cup electrodes).

Figure 2:
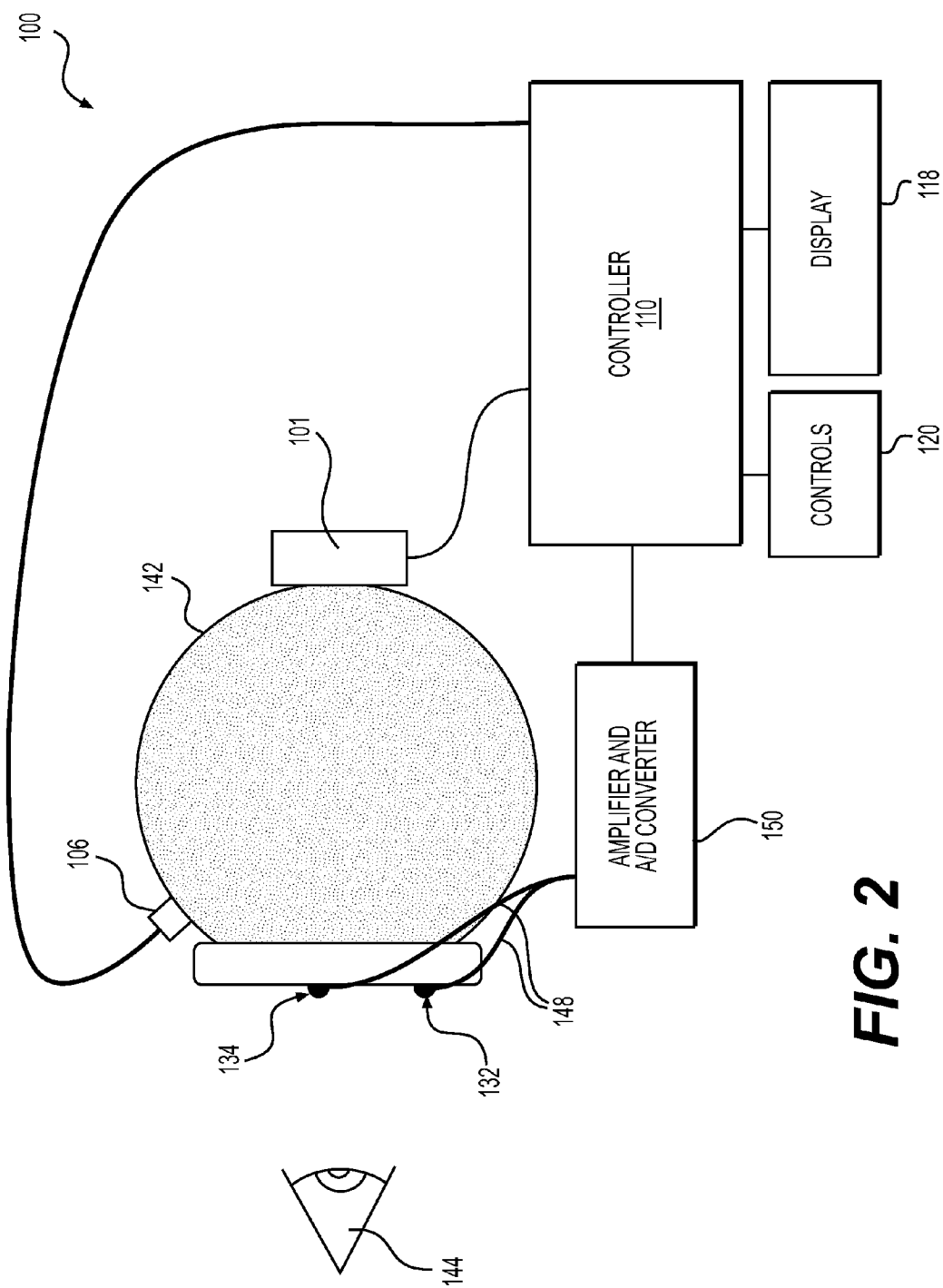
FIG. 2 is a schematic view illustrating components contained within the visual electrophysiology device of FIG. 1

FIG. 2 depicts a schematic illustration of components that may be contained within the device 100 of FIG. 1 as previously shown in U.S. Pat. No. 7,540,613. In FIG. 2, the light emitter 106 provides a light stimulus to the eye 144. Current high brightness LED's have sufficient brightness for carrying out the present invention with an efficient diffuser, however, in certain applications a plurality of LEDs may be used for a light emitter 106.

A light emitter 106 is controlled by a controller 110 that provides the overall control of the device 100. Controller 110 may be a microcontroller or microcomputer device with a processor, memory and other connections to other components of device 100. Controller 110 may be a pre-programmed computer that is programmed to perform the functions and controls described herein. Alternatively, controller 110 may include wireless connections or wired connections that allow remote programming (e.g., for additional functions or updates). Those of ordinary skill in the art would understand how to program and operate controller 110. Control of the light emitter 106 is by means of the controller 110 which can control the timing of the firing of the light and camera sources, as well as the intensity, frequency and synchronicity thereof as further described below. By way of example, the controller 110 can modulate the activity of the light emitter 106, such as an LED to provide a series of brief flashes of light of predetermined duration, however, other stimulus waveforms or stimulus frequencies can also be utilized as further described below.

The light emitter 106 is positioned so as to emit light to the interior of a diffuse spheroidal reflector 142 so that the light from the light source is directed uniformly toward the eye 144 from all directions. In the illustrated embodiment, the diffuse spheroidal reflector 142 is spheroidal in configuration with a white interior surface to enhance the reflectivity. The white surface can be a coating (e.g., paint) or diffuse spheroidal reflector 142 can be made for example, from white plastic. The use of the diffuse spheroidal reflector 142 provides an even illumination to most of the retina of the eye 144. Diffuse spheroidal reflector 142 is an exemplary optical assembly 104.

Returning to FIG. 2, as previously explained, the light stimulus by the light emitter 106 gives rise to an electrical signal from the eye 144 that can be sensed by e.g., electrodes 132, 134 contacting the skin of the patient proximate to the eye 144, whereby the electrical signal is communicated by wires 148 to an amplifier and an analog to digital (A/D) converter shown as block 150. The A/D converter (located for example on the electronics board 109 in FIG. 1) can measure the electric signals on the electrodes and provide the information to the controller 110. The controller 110 can analyze the electric signals so as to provide an indication of visual system function, using techniques described for example, in the references cited in the Background section above.

The analysis of the data from the electrical signals sensed by the electrodes 132, 134 is, as described, carried out by the controller 110. Algorithms for specifically assessing retinal ischemia in a patient have been published. See, for example, Severns et al. (1991), Severns and Joshson (1991), and Kjeka et al. (2013). For other diseases, algorithms are described in the references cited in the Background section above.

In exemplary embodiments, signals from the skin electrodes 132, 134 are analyzed for the amount of noise present to determine if accurate and clinically meaningful measurements can be made. If the signal to noise ratio is marginal, additional data can be collected to improve the estimate. Next, a sine wave is fit to the data to determine the amount of elapsed time between the actuation of the stimulus and the maximal response of the eye. This measurement has been shown to be a highly sensitive measure of the extent of ischemia in the eye (Severns et al. (1991)).

As further components of the device 100, (FIG. 1) there are controls 120 that can be used to initiate each test and to enter customized settings. In addition, the device 100 can provide a visual readout 118 to the user of the results of each test, that is, the readout 118 provides a visual readout to the user that is related to the amount of retinal ischemia of the eye.

The amplifier can be a biomedical amplifier using 24 bit (or more) A/D converters that eliminates gain adjustment and the prolonged recovery from saturation of conventional amplifiers. Typically, conventional amplifiers have required some oversight by a technician during testing to assure that the gain setting was correctly matched to the input range of the A/D converter. Further, such conventional amplifiers could saturate (fail to respond to the input signal) and might take tens of seconds to recover the ability to respond to a signal. The saturation is difficult to distinguish from a lack of response from the patient making reliable automation of signal acquisition difficult.

To avoid such problems, the device 100 may utilize a low gain differential amplifier (no more than 32×) and a high resolution (typically 18 bits or greater) differential A/D converter to acquire the signal from the eye 144 by means of the skin electrodes 132, 134. Thus, the amplifier has a very high tolerance for noise and offsets, while producing highly faithful reproduction of the input waveform. The amplifier and A/D converter of block 150 are also immune to prolonged saturation caused by interfering signals. In some embodiments, the amplifier and A/D converter can be built into the same device (e.g., an ADS1220, ADS1248, ADS1292, ADS1294, ADS1298, or ADS1299 from Texas Instruments or an AD7195, AD7194, AD7193, AD7799, AD7738 from Analog Devices to name a few). Some embodiments do not use an amplifier. Input impedance of the system is very high (>10 MΩ) so that the relatively high impedance of the electrodes 132, 134 contacting the skin does not affect the results. The output of the A/D converter in block 150 is connected to the controller 110, which analyzes the data.

Conveniently, all the electrodes used for one eye can be located in a self-adhering electrode array such as those described in U.S. Provisional Patent Application Ser. No. 61/696,499, filed Sep. 4, 2012 and PCT Application Serial No. PCT/US13/58007, filed Sep. 4, 2013, the disclosures of which are expressly incorporated by reference herein. In some embodiments, three electrodes are used in an array for each eye. An A/D converter (located for example on electronics board 109) can measure the electric potential difference between a first electrode and a second electrode in the electrode array, and a common-mode attenuation circuit can be electrically connected to a third electrode in the electrode array. An advantageous and novel arrangement of these electrodes is where the distance between the first and second electrode is greater than both the distance between the first electrode and third electrode and the distance between the second electrode and third electrode. As a result, the common-mode attenuation circuit can be considered connected to the middle of the three electrodes.

In contrast, current practice (as described in the ISCEV standard Marmor et al. (2009)) uses remote locations such as the earlobe for a common-mode attenuation circuit electrode location. When electrodes are located on a small sensor array, however, the performance is improved by maximizing the distance between the first and second electrode. For example, in one embodiment, the first electrode can be located under the eye, the second electrode can be located near the temple, and the third electrode can be located in between the first electrode and the second electrode. The common-mode attenuation circuit can reduce the common-mode voltage difference between signals on the electrodes and the A/D converter caused, for example, by capacitive coupling between the power lines and the body. By reducing common-mode interference, potential measurements between electrodes can be made more accurately. Exemplary common-mode attenuation circuits include a right leg drive circuit and a constant potential with respect to a potential at the A/D converter.

An electronics board 109 may have a controller 110 modulating a light emission from the first light emitter to create a first flash of light having a duration less than 21 ms. The controller 110 may also modulate a light emission from the second light emitter to create a second flash of light having a duration less than 21 ms. The controller 110 may also modulate a light emission from the third light emitter to create a third flash of light having a duration less than 21 ms. Generally, the controller 110 modulates a light emission from one or more light emitters to create flashes of light having durations less than 21 ms, for example, less than 10 ms, 6 ms, 5 ms, 4 ms, or 3 ms.

When constructing flashes of light from multiple different colored sources, there are several alternative ways to do so. For example, if the first light emitter emits green and the second emitter emits blue, then to emit the color cyan, both emitters are needed. A common way is to control the flash duration for each source independently. For example, the green flash duration may be 2 ms and the blue flash duration 5 ms. The starting times for the two flashes may be aligned, or the ending times may be aligned, or to reduce the peak electrical power requirements, the second flash may begin soon after the first completes. Because the flashes are short, even though the durations differ, they are perceived by the brain as a cyan color. However, the retina responds to the light as it arrives, leading to millisecond-level uncertainties in when should the flash be considered to have occurred (in the present example). Analogous statements can be made if white light is synthesized from red, green, and blue LEDs. One common visual electrophysiology test, the 30 Hz flicker electroretinogram (Marmor et al. (2009)), has response times in the range of 20-40 ms, where a few milliseconds of uncertainty caused by the flash characteristics may produce errors in the measurements.

Nevertheless, appropriately synthesized colors have advantages over single LEDs. Two methods of creating a white flash, for example, are by using a white light source (e.g., a white LED or xenon bulb) or by synthesizing the color using, for example, red, green, and blue LEDs. The optical assembly 104 may reflect some wavelengths better than others, leading to deviations from the spectrum of a white light source. The color of the optical assembly 104 may also change from part-to-part due to manufacturing variation, leading to part-to-part deviations in the spectrum emitted if a white light source is used. In contrast, the color can be tuned to the desired color, independent of the exact color absorption of the optical assembly 104, when using red, green, and blue LEDs.

One method to reduce the timing uncertainty caused by flash characteristics is to have the light waveforms overlap in time. In some embodiments, the independent visible light spectral sources overlap by at least 50%, 60%, 70%, 80%, 90%, 95%, or 99% of the longer of the flashes (whether it be 2, 3, 4, or more independent visible light spectral sources). FIG. 4 shows an overlap of 100%, where all the lights flash simultaneously. Some embodiments use light flashes that are symmetric about a center point. For example, a 2 ms blue flash can be combined with a 4 ms green flash by having the blue occur in the interval (t−1 ms, t+1 ms) and the green flash over the interval (t−2 ms, t+2 ms). Thus, the center of each flash occurs at the same time (t ms in this example). One method to achieve the desired color without affecting the percentage overlap is to individually adjust the current applied to each source. Brightness can be adjusted either by further current adjustments or the duration of the flash can be changed.

An infrared light emitter 103 may be optionally used to image the eye in the infrared spectrum. Contrast between the pupil and the iris may be improved with infrared illumination. The controller 110 modulates a light emission from an infrared light emitter 103 to create an infrared flash of light having a duration less than 40 ms, 30 ms, 20 ms, 10 ms, 5 ms, or 3 ms. The exact duration of the infrared flash may be constant, or may dynamically change in operation to provide varying exposures in camera 101. A typical exposure time in some embodiments can be 2.6 ms. However, the exposure time may be varied by the controller 110, for example, based on feedback from sensors.

Generally, a shorter exposure time can be better because images have less motion blur and are less affected by external light, but shorter exposure times also increase the peak electrical power demands of the device 100 and provide less light to the camera 101.

In some embodiments, it is advantageous to minimize the energy emitted by the visible light stimulus to the retina when the infrared light is flashed on and off. First, peak power required by the device 100 is reduced by having light emitted from the light emitter 106 and infrared light emitter 103 occur at substantially different times. Additional advantages exist when the camera 101 acquires images during IR flashes. If the visible light during an IR flash is small, then chromatic aberrations in the images taken by the camera 101 are also small as the spectral content of the illumination is more limited. Moreover, if the visible light during an IR flash is small, the camera 101 can acquire images primarily in the infrared, which may improve contrast between the pupil and the iris, even if the camera 101 is sensitive to visible and IR light. It may be advantageous to have the camera 101 sensitive to both visible and infrared light in order to reduce cost and/or so that the camera 101 can provide visible-light features to the device 101, such as reading information off of computer displays, smartphones, and the like.

Some embodiments with the optional infrared light emitter 103 do not have a camera 101; these embodiments may use the infrared light, for example, to trigger other devices by providing synchronization information.

The energy emitted by the first light emitter during the infrared flash of light can be less than 50%, 40%, 30%, 25%, 20%, 10%, 5%, or 1% of the energy emitted by infrared light emitter during the infrared flash of light. Similarly, in embodiments having a second light emitter, the energy emitted by the second light emitter during the infrared flash of light may be less than 50%, 40%, 30%, 25%, 20%, 10%, 5%, or 1% of the energy emitted by the infrared light emitter during the infrared flash of light.

Figure 4A:
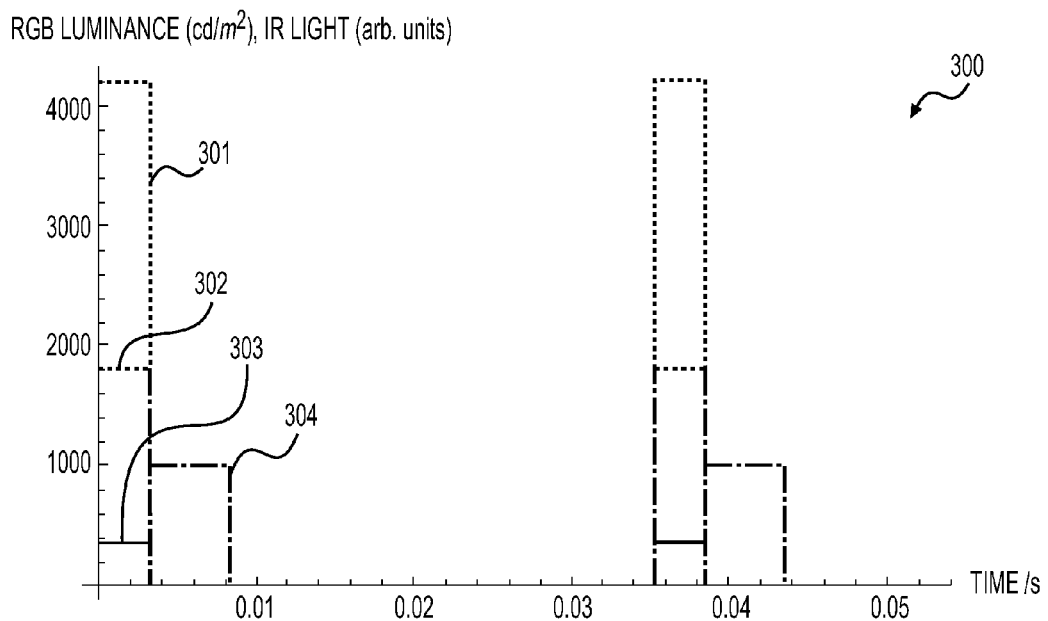
FIG. 4A shows a periodic synthesized white light stimulus followed by an infrared flash.
Figure 4B:
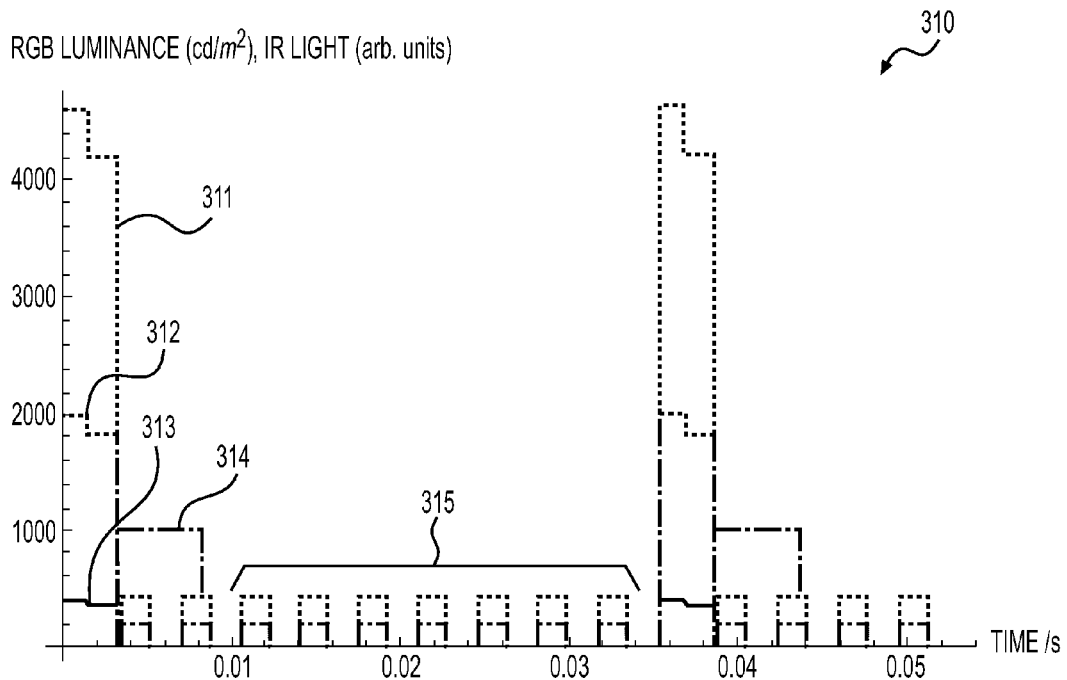
FIG. 4B shows a periodic synthesized white light stimulus followed by an infrared flash, with a superimposed higher-frequency synthesized white light background.

In some embodiments, the first light emitter emits 0% of the energy emitted by the infrared light emitter during the infrared flash of light to minimize chromatic aberrations and to provide better contrast in the IR, as shown in FIG. 4A. If background illumination is used (e.g., as shown in FIG. 4B), then some visible light during the infrared may be difficult to avoid and the percentage will be higher than 0%. Similarly, in embodiments having a third light emitter, the energy emitted by the third light emitter during the infrared flash of light may be less than 50%, 40%, 30%, 25%, 20%, 10%, 5%, or 1% of the energy emitted by infrared light emitter during the infrared flash of light.

The controller 110 can modulate a light emission from the first light emitter to create a light stimulus having a stimulus frequency greater than 7 Hz, including but not limited to the list of frequencies near 30 Hz enumerated below. The controller 110 may also modulate a light emission from the infrared light emitter 103 to create infrared flashes of light having durations less than 40 ms and an infrared flash frequency greater than 1 Hz.

In some cases, controlling the timing between the stimulus frequency and the infrared flash frequency can be advantageous so that, for example, the lighting created by the light stimulus interacts in a consistent manner with the infrared flashes. Other potential advantages of controlling the timing between the two frequencies include reduced peak power, better contrast with less chromatic aberration and less changes to lighting levels in embodiments using a camera sensitive to visible and IR light. Without time synchronization, lighting levels in embodiments using a camera sensitive to visible and IR light will vary at the beat frequency between the visible and infrared light frequencies.

In some embodiments, the energy emitted by the first light emitter during the infrared flashes of light is less than 50% of the energy emitted by infrared light emitter during the infrared flash of light, and the ratio of the stimulus frequency to the infrared flash frequency is within 1% of an integer or within 1% of the reciprocal of an integer, for example, the ratio can be 1.

The light emitter 106 generates visible light that can stimulate the visual system of a patient. In some embodiments, the light emitter 106 creates a light stimulus that occurs on a periodic basis having a stimulus frequency within 0.01 Hz of one of the following frequencies: 26.94, 27.13, 27.32, 27.51, 27.70, 27.90, 28.10, 28.31, 28.51, 28.72, 28.94, 29.15, 29.37, 29.59, 29.82, 30.05, 30.28, 30.52, 30.76, 31.00, 31.25, 31.50, 31.76, 32.02, 32.28, 32.55, 32.83, 33.10, 33.67 Hz, or integer multiples thereof. Other frequencies may be used.

In some embodiments, the light emitter 106 creates a light stimulus having a stimulus frequency within 0.1 Hz of 28.31, 28.72, or 32.55 Hz, or integer multiples thereof. The light emitter 106, can creates flashes at a sufficiently large frequency (e.g., above about 50 Hz) so that the light appears to be constantly on. In some embodiments, the frequency is lower than 40 Hz and may appear to flash or flicker. In other embodiments, the light emitter 106 creates flashes at a frequency above about 50 Hz and additional light at a frequency lower than 40 Hz, creating the appearance of a flickering light on top of a constant background. For example, the device 100 can create a flickering light at a frequency within 0.01 Hz of 28.31 Hz and a perceptually-constant background at a frequency within 0.1 Hz of 283.06 Hz. In some embodiments, the light emitter 106 generates a light stimulus having a stimulus frequency greater than 7 Hz.

FIG. 4 shows exemplary timing diagrams for light waveforms described above. Plot 300 shows 1.5 periods of synthesized white light flash followed by an IR flash. Both the synthesized white light flash (also referred to as the stimulus) and IR flash occur at a stimulus frequency of about 28.306 Hz. Consequently, the ratio of the visible light flash frequency and the infrared light flash frequency is 1. Curve 301 depicts the luminance output of a green LED that is part of the light emitter 106, as measured at the eyecup 107. Curves 302, 303 depict the corresponding luminance outputs from red and blue (respectively) LEDs that are also part of the light emitter 106 measured at the eyecup 107. Curve 304 depicts output from the infrared light emitter 103. In this example, there is no overlap between the output of visible light and infrared light.

Plot 310 is analogous to plot 300, with the exception the addition of a background illumination. The background illumination is created in this example with 283.06 Hz flashes of the red, green, and blue LEDs, 7 of which are indicated by designator 315. The 283.06 Hz background frequency is higher than the patient's critical fusion frequency and thus is perceived to be a constant illumination. While in this example, the background frequency is 10 times the stimulus frequency, other multiples are contemplated as well (including multiples of 2, 3, 4, 5, 6, 7, 8, 9, 11, 12, 13, 14, 15, 16, 17, 18, 19, 20, or more). The red, green, blue, and infrared waveforms are indicated with the same dashing patterns as in plot 300, and with the designators 312, 311, 313, and 314 respectively. In the example shown in plot 310, 2 of the background flashes occur during the infrared light emission and 1 of the background flashes occurs during the stimulus flash. The same or different light emitters can be used to create the background and stimulus illumination.

A camera 101 may be optionally used to image the eye of the patient periodically at a frame rate frequency. A controller 110 in the device 100 can use the images, for example, to detect the eye's pupil and measure its area. If the pupil cannot be detected, the device 100 may be configured to not present results as a safeguard to reduce the likelihood of presenting erroneous results. Alternatively, the device 100 may present results irrespective of a pupil being detected, which may be advantageous in cases such as stimulating the eye through a closed eyelid.

In certain embodiments, the controller 110 may modulate a light emission from the first light emitter creating a light stimulus having a stimulus frequency greater than 7 Hz, including but not limited to the list of frequencies near 30 Hz enumerated earlier in this disclosure. In some cases, controlling the timing between the stimulus frequency and the frame rate can be advantageous so that, for example, (a) the lighting created by the light stimulus interacts in a consistent manner with the image acquisition by the camera 101, and/or (b) updates to stimulus luminance based on pupil area measurements happen in a consistent manner.

In some embodiments, the ratio of the stimulus frequency to the frame rate is within 1% of an integer or within 1% of the reciprocal of an integer, for example, the ratio can be 1. In some embodiments, the ratio of the stimulus frequency to the frame rate is greater than 7, for example, 8, 9, 10, 11, 12, 13, 14, 15, or more. High ratios can occur (but are not required to occur), for example, when using pulse-width modulation to create light stimuli that approximate a retinal irradiance that varying as a sinusoid, a square wave having a duty cycle between 30% and 70%, or a triangular wave. Further, when using a camera 101 with an infrared light emitter 103 to image the eye in the infrared, the frame rate may equal the flash rate from the infrared light emitter 103 (i.e., 1 IR flash per image) and the ratio of these rates to the stimulus frequency can be 1% of an integer or within 1% of the reciprocal of an integer (for example, 1).

Using the camera 101, a controller 110 in the device 100 can measure the area of the patient's pupil. With this information, the controller 110 can adjust light stimulus as a function of the area. This adjustment may be useful, for example, to reduce the intra-patient and/or inter-patient variability that results from differences in retinal illumination caused by variations in pupil area. The adjustment of the light stimulus as a function of pupil area can occur at the frame rate frequency and/or other frequencies such as a frequency faster than 0.5 Hz, 1 Hz, 2 Hz, 5 Hz, 10 Hz or 20 Hz. The adjustment of the light stimulus as a function of the pupil area does not have to happen on a periodic basis; for example, a microprocessor on the controller may have a peak CPU load greater than 100% which causes an adjustment to be occasionally missed. As shown in Satoh et al. (1994), the timing of the response to a 30 Hz flicker stimulus depends on the intensity of the light. In Satoh et al. (1994), the eyes were dilated and an artificial pupil having a diameter of 5 mm was inserted so as to make the stimulus pupil size independent.

Figure 3A:
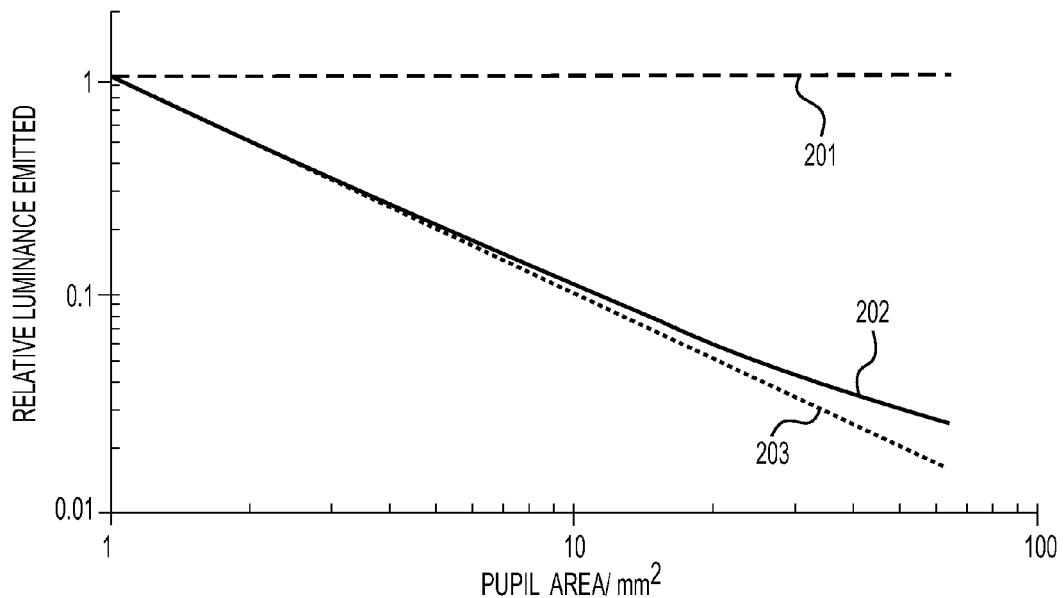
FIG. 3 shows three exemplary relations between luminance and pupil area, from the perspective of luminance emitted from the visual electrophysiology device (FIG. 3A) and of retinal illuminance (FIG. 3B).
Figure 3B:
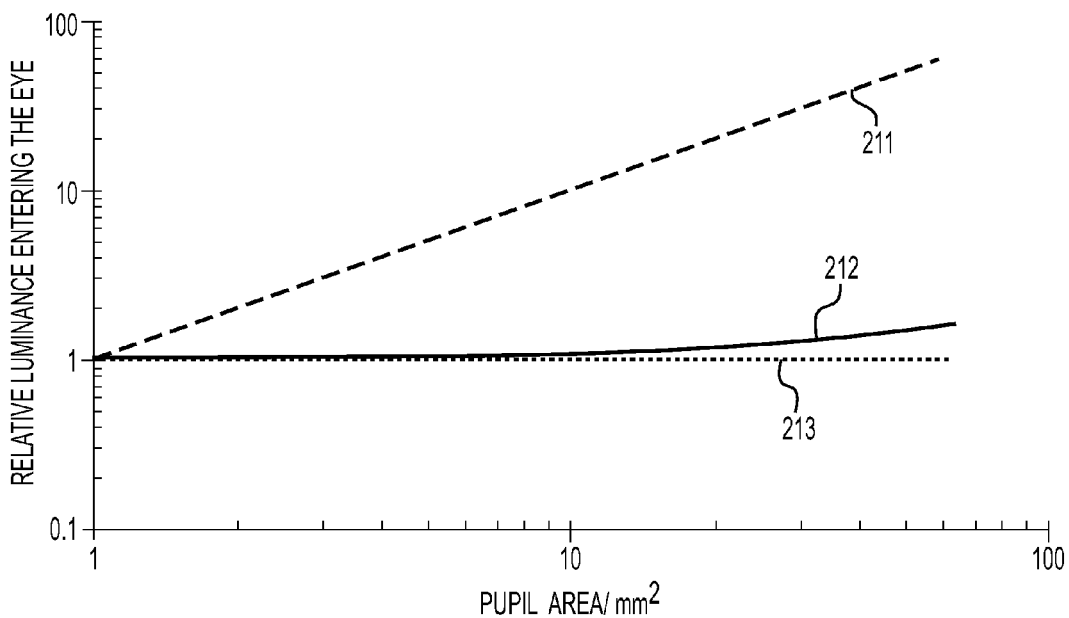

Exemplary relations between luminance of the visual stimulus and the pupil area are shown in FIG. 3, where FIG. 3A shows the relation between the light emitted from the device 100 and pupil area; FIG. 3B shows the relation between retinal illuminance and pupil area. Curve 201 shows a flash luminance that is independent of pupil area. In this case, as shown by Curve 211, the total amount of light entering the eye changes linearly with pupil area. In some embodiments, the light stimulus can be linearly related to the multiplicative inverse of the eye's pupil area. For example, the light stimulus can be made so that the energy entering the eye is constant, independent of pupil size. Curves 203 and 213 show this relation, where the amount of light entering the eye is constant.

In other embodiments, the light stimulus can be related to the multiplicative inverse of the eye's pupil area through a non-linear, concave function. Using a non-linear concave function can compensate for the eye's reduced sensitivity to light entering away from the center of the pupil (e.g., the Stiles-Crawford effect). In these cases, the amount the light is reduced as the area increases is smaller than the amount that the pupil area increased. Curves 202 and 212 show this relation, where the amount of light entering the eye increases slowly with pupil area, as the effectiveness of stimulating the retina is reduced for light not entering the center of the pupil.

In some embodiments, the device 100 may measure the area of the patient's pupil. In cases where the area of the pupil cannot be measured (for example, because the eyelids are closed), the controller 110 may estimate the pupil size based on previous measurements. If the pupil has not yet been identified, the controller may indicate so to the device operator and not provide a result (i.e., an indication of visual system function). The controller 110 may be arranged so as to wait indefinitely or for a predetermined amount of time before the initial pupil acquisition before proceeding with the remainder of the test process. This fail-safe procedure helps prevent erroneous results. Additionally, if the pupil size has been measured but has subsequently been lost and not been measured for at least a predetermined amount of time (e.g., 0.1, 0.2, 0.3, 0.4, 0.5, 0.6, 0.7, 0.8, 0.9, 1 second or more), the controller 110 may also indicate an error to the device operator and not provide a result.

In some embodiments, the device 100 has a light detector 105 that can monitor the output of the light emitter 106. The light detector 105 can comprise, for example, a photodiode. The light detector 105 can also monitor the amount of light originating outside the device 100 that enters the optical assembly 104 (herein called "external light"). The light detector 105 can generate an expected set of signals, based for example on expected levels of external light and/or expected levels of the light emitter 106. If these expectations are not met, the controller 110 may not provide a result.

Certain visual tests depend on the amount of background illumination. If the eyecup 107 is pressed against the skin surrounding the eye to be tested, the amount of external light is reduced. Nevertheless, some external light may be present and act as additional background illumination. If the amount of external light exceeds a threshold, the light detector 105 can be used to detect this case to prevent providing erroneous results. For example, the threshold can be between 1 $cd/m^2$ and 200 $cd/m^2$. The threshold can be between 3 $cd/m^2$ and 30 $cd/m^2$. The threshold can be between 10 $cd/m^2$ and 100 $cd/m^2$.

The amount of external light may be combined with information regarding the pupil size of the eye being tested to determine if the amount of external light is too large. For example, the threshold can be a value between 10 Td and 1000 Td. The threshold can be a value between 30 Td and 300 Td. In some embodiments, the threshold can also depend on the stimulus. For example, dimmer stimuli may require a lower threshold.

In some embodiments, the amount of external light can be used to modify the stimulus in order to reduce the effect of external light on the electrical measurement.

The optional light detector 105 may be used to monitor the light stimulus so that the controller 110 can compensate for variations in the output of the light emitter 106 or the optical efficiency of the optical assembly 104. The controller 110 can adjust, for example during a calibration phase of a test, the output of light emitter 106 in order to achieve a desired signal from light detector 105. If the adjustment is too great, the device 100 may be configured to report an error rather than possibly providing erroneous results.

In some embodiments, the device 100 has an electrical impedance meter measuring the impedance associated with the electrical signal received from the visual system of the patient attached through the patient connector 108. If the impedance is too large, the device 100 may not be electrically connected to the patient or the connection may be of such a poor quality as to comprise the signal quality. In some embodiments, the controller 110 does not provide an indication of visual system function unless the impedance is less than a target value, such as 1 GΩ, 500 MΩ, 150 MΩ, 15 MΩ, 1.5 MΩ, 150 kΩ, 100 kΩ, 50 kΩ, 25 kΩ, 10 kΩ, or 5 kΩ. The high end of these values (e.g., 1 GΩ, 500 MΩ, 150 MΩ, or similar) enables embodiments to reveal whether or not something is connected. If impedance down near the lower end is utilized, the embodiments may indicate that an effective connection with little noise has been made. However, achieving the lower end of impedance may not be reasonably practicable or worthwhile because of the skin preparations required to get that low of an impedance. In some embodiments, the impedance near the high end (150 MΩ) is sufficient. Other embodiments may require a lower impedance.

Figure 5A:
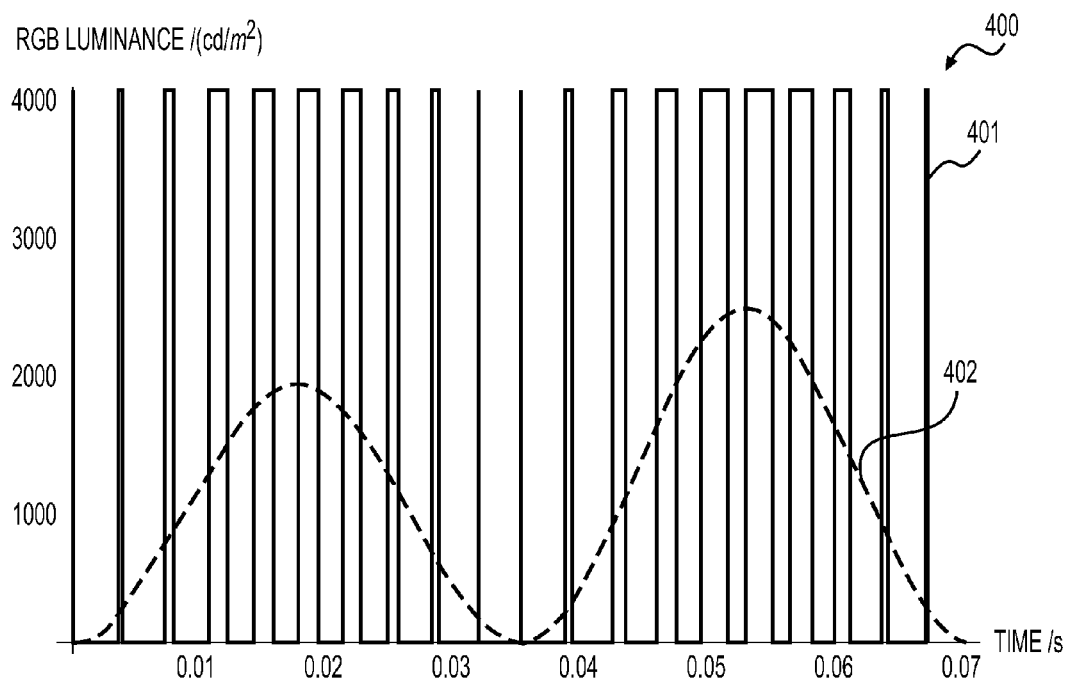
FIG. 5A shows a desired sinusoidal waveform and a pulse-width modulation (PWM) approximation thereof.

Turning to FIG. 5, three exemplary timing diagrams for light waveforms are shown. In FIG. 5A, Plot 400 shows 2 periods of synthesized white light, occurring at a stimulus frequency of about 28.306 Hz. Curve 402 represents the desired sinusoidal stimulus while pulse train 401 represents a pulse-width modulation (PWM) approximation to curve 402. In this example the PWM period is 10 times the stimulus period; however, other ratios of stimulus period to PWM period are contemplated, including ratios greater than or equal to 7. In some embodiments, integer ratios are preferred because each period is thereby more similar to each other. Curve 402 shows 2 periods, however, the amplitude of the 2 periods are not the same.

As described above, using the camera 101, a controller 110 can measure the area of the patient's pupil. With this information, the controller 110 can adjust the luminance as a function of the area. Between the first and second period of curve 402, the device 100 measured the pupil to be smaller and therefore increased the brightness of the desired light waveform in order to reduce the effect of pupil size on retinal stimulation.

Figure 5B:
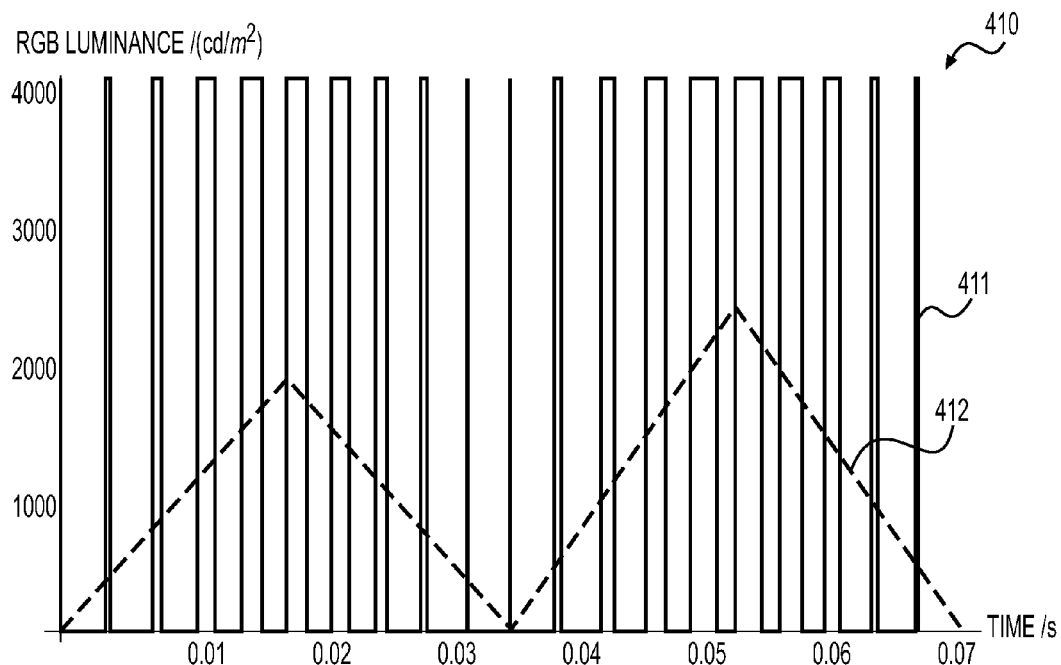
FIG. 5B shows a desired triangular waveform and a PWM approximation thereof.
Figure 5C:
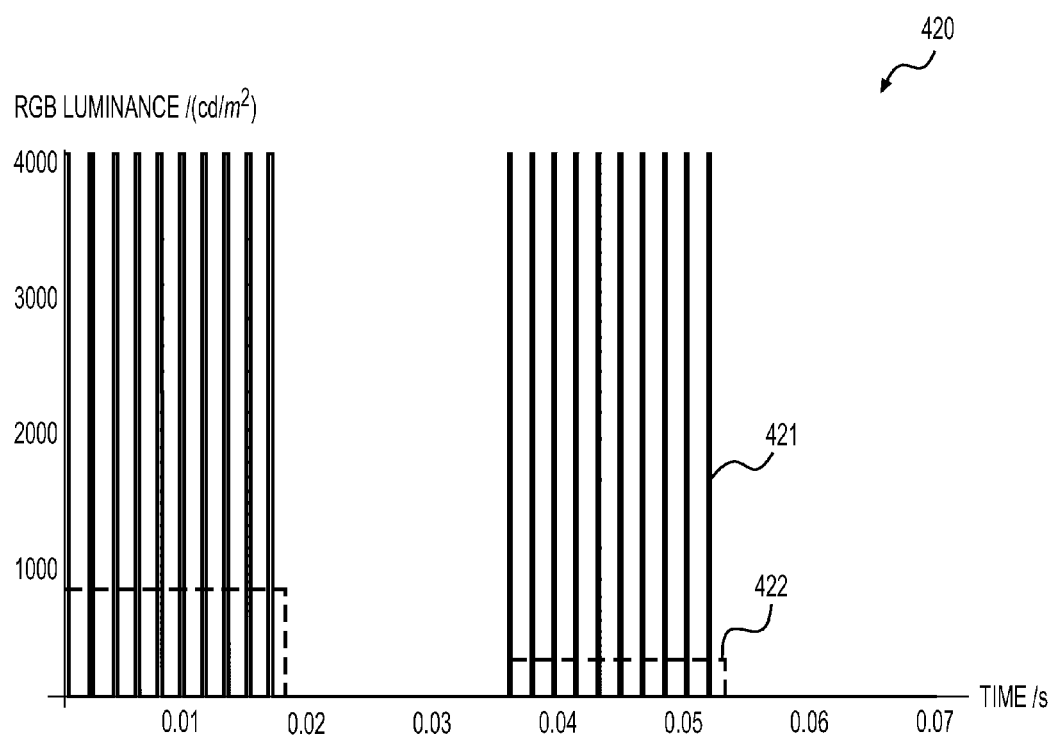
FIG. 5C shows a square waveform and a PWM approximation thereof.

In FIG. 5B, Plot 410 is analogous to Plot 400, except the desired light waveform is a triangular wave. Curve 412 is the desired triangular wave and pulse train 411 is the PWM approximation thereof. In FIG. 5C, Plot 420 is also analogous to Plot 400, except a square wave is the desired light waveform. Curve 422 is a 50% duty cycle square wave. Other duty cycles are also contemplated, for example square waves having a duty cycle between 30% and 70%, and square waves having a duty cycle between 40% and 60%. Short duty cycles (e.g., <20%) may be implemented with a single flash such as shown in FIG. 4.

Pulse train 421 is a PWM approximation to Curve 422. In this example, the stimulus period is 20 times the PWM period. Curve 422 has the second period being smaller in amplitude than the first, which may occur, for example, when the device 100 measures an increase in pupil area. In some embodiments, the device 100 directly synthesizes a continuous light waveform that approximates a retinal irradiance that varies as one of a sinusoid, a square wave having a duty cycle between 30% and 70%, or a triangular wave.

In some embodiments, the device 100 uses pulse-width modulation (PWM) to create a light stimulus approximating a retinal irradiance varying as one of a sinusoid, a square wave having a duty cycle between 30% and 70%, or a triangular wave. For example, the controller 110 can use PWM to control the output of a first light emitter and a second light emitter in order to deliver a periodic visual stimulus to the eye approximating a retinal irradiance varying as one of a sinusoid, a square wave having a duty cycle between 30% and 70%, or a triangular wave. For example, the controller 110 can use PWM to control the output of a first light emitter and a second light emitter in order to deliver a periodic visual stimulus to the eye approximating a retinal irradiance varying as a sinusoid.

The controller 110 in the electronics board 109 can be any of those known in the art. The controller 110 can be a single microprocessor, for example, one sold by Analog Devices, Atmel, Intel, Microchip, Texas Instruments, etc. Alternatively, the controller 110 can be distributed among many integrated circuits on one or more printed circuit boards in the device 100. The controller 110 can be configured to modulate the light output of a first light emitter and to receive and analyze the electrical signal from a patient.

In some embodiments, the controller 110 can communicate with a camera and measure the pupil size in images taken with the camera. In some embodiments, the controller 110 can modulate the light output from additional light emitters, such as a second light emitter, a third light emitter, and/or an infrared light emitter. The controller 110 can provide to the operator an indication for visual system function of a human using a display and/or providing a means to communicate the information to a computer or other electronic device.

While the above descriptions have emphasized compositions, methods of their use are also contemplated. To provide an indication of visual system function, the methods involve illuminating an eye of the patient with a light stimulus. The methods also involve either receiving and analyzing an electrical signal from the patient so as to provide an indication of visual system function or measuring the electric potential difference between a first electrode and second electrode so as to provide an indication of visual system function.

Illuminating the eye may comprise visible flashes of light having a duration less than 21 ms from 1, 2, 3, or more distinct spectral sources. When these flashes of light come from a plurality of spectral sources, they can be configured to overlap in time by at least 50%, 60%, 70%, 80%, 90%, 95%, or 99% of the longest of the flashes so as to reduce the timing uncertainty as described earlier in this disclosure.

The methods may involve measuring the eye's pupil area and adjusting the energy in the first flash (or other light stimuli) as a function of the eye's pupil area, for example, wherein the energy in the first flash is linearly related to the multiplicative inverse of the eye's pupil area or wherein the energy in the first flash is related to the multiplicative inverse of the eye's pupil area through a non-linear, concave function. In some methods, the light stimulus comprises flashes of light having a flash frequency greater than 7 Hz and the measuring of the eye's pupil area occurs at a frame rate wherein the ratio of the flash frequency to the frame rate frequency is within 1% of an integer or within 1% of the reciprocal of an integer—these features may occur separately or together with the overlapping flashes described above. In some methods, the light stimulus comprises flashes of light having a flash frequency greater than 7 Hz and the eye is also illuminated with infrared flashes of light that have most of their energy emitted at wavelengths longer than 710 nm, wherein the infrared flash frequency is greater than 1 Hz, wherein the energy emitted by the first light emitter during the infrared flash of light is less than 50% of the energy emitted by infrared light emitter during the infrared flash of light, and wherein the ratio of the stimulus frequency to the infrared flash frequency is within 1% of an integer or within 1% of the reciprocal of an integer—these features may occur separately or in any combination of frame rate and overlapping flash methods described above.

Some methods involve placing an electrode array comprising three electrodes on the skin of the patient as a single unit, wherein the three electrodes include a first electrode, a second electrode and a third electrode, wherein the first and second electrode are more distant from each other than any other pairing of the first, second, and third electrodes, which can occur separately or in any combination with infrared flashing, frame rate, and overlapping flash methods described above.

Some methods involve measuring the eye's pupil area and adjusting the luminance of the light stimulus through a non-linear, concave function of the eye's pupil area, which can occur separately or in any combination with the electrode array, infrared flashing, frame rate, and overlapping flash methods described above. Some methods involve measuring the eye's pupil area and adjusting the luminance of the light stimulus as a function of the eye's pupil area, wherein the light stimulus that approximates a retinal irradiance that varies as one of a sinusoid, a square wave having a duty cycle between 30% and 70%, or a triangular wave, which can occur separately or in any combination with the electrode array, infrared flashing, frame rate, and overlapping flash methods described above.

Some methods include techniques to reduce erroneous results, each of which can be used separately or in combination with any of the other methods. Some methods include attempting to locate the eye's pupil in images taken by a camera and not returning an indication of visual system function unless the eye's pupil has been identified. Some methods include receiving a signal from the light detector and not returning an indication of visual system function if the signal from the light detector differs from a set of expected light detector signals, wherein the set of expected light detector signals comprises monitoring for external light exceeding a threshold. The threshold can be any of those described above, including those dependent and independent of pupil area. Some methods include measuring the eye's pupil area and adjusting the luminance of the light as a function of the eye's pupil area, and measuring an electrical impedance associated with the electrical signal received from the patient, wherein the indication is not provided unless the electrical impedance meter measures an impedance smaller than a target value. The target value can be any of those described above, including those in the G$\Omega$, M$\Omega$, and k$\Omega$ range.

All references cited herein are incorporated by reference in their entirety. To the extent publications and patents or patent applications incorporated by reference contradict the disclosure contained in the specification, the specification is intended to supersede and/or take precedence over any such contradictory material.

All numbers expressing quantities used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description of devices includes many novel and advantageous aspects. Combinations of the aspects are also contemplated. It will be apparent to those skilled in the art that various modifications and variations can be made in the disclosed detection device, components, and methods without departing from the scope of the invention. Other embodiments of the invention will be apparent to those skilled in the art from consideration of the specification and practice of the invention disclosed herein. It is intended that the specification and examples be considered as exemplary only, with a true scope of the invention being indicated by the following claims and their equivalents.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated.

CITED REFERENCES

Bresnick, George, and Mari Palta. (1987) "Temporal Aspects of the Electroretinogram in Diabetic Retinopathy." Arch Opthalmol, 105:660-4.

Han, Young-Keun, and Young-Hoon Ohn. (2000) "Changes of ERG Parameters in Diabetic Retinopathy." J Korean Ophthalmol Soc, 41:149-155.

Holder, Graham, et al. (2007) "ISCEV standard for clinical pattern electroretinography—2007 update." *Doc Ophthalmol,* 114:111-116.

Hood, Donald, et al. (2012) "ISCEV standard for clinical multifocal electroretinography (mfERG) (2011 edition)." *Doc Ophthalmol,* 124:1-13.

Kjeka, O, R W Jansson, C Bredru, and J Krohn. (2013) "Early panretinal photocoagulation for ERG-verified ischaemic central retinal vein occlusion." *Acta Ophthalmol,* 37-41.

Marmor, M F, et al. (2009) "ISCEV standard for full-field clinical electroretinography (2008 update)." *Doc Ophthalmol,* 118:69-77.

Odom, Vernon, et al. (2010) "ISCEV standard for clinical visual evoked potentials. (2009 update)." *Doc Ophthalmol,* 120:111-119.

Satoh, S, H IIjma, M Imai, K Abe, and T Shibuya. (1994) "Photopic electroretinogram implicit time in diabetic retinopathy." *Japanese Journal of Ophthalmology,* 38: 178-184.

Severns, M L, Johnson, M A and Merritt, S A. (1991) "Automated estimate of implicit time and amplitude of the flicker electroretinogram." *Applied Optics* 30:2106-2112.

Severns, M L and Johnson, M A (1991) "Automated implicit time and amplitude determination for the 30 Hz flicker electroretinogram: performance prediction of neovascularization central retinal vein occlusion." *Technical Digest Series,* Washington, D.C.; Optical Society of America, pp. 10-13.

Shapiro, A G, Pokorny J, and Smith V C. (1996). "Cone-rod receptor spaces with illustrations that use CRT phosphor and light-emitting-diode spectra." *J. Opt Soc. Am. A.*, 2319-2323.

The invention claimed is:

1. A device providing an indication of visual system function of a patient comprising:
   a. a first light emitter having a visible first emission spectrum;
   b. an optical assembly arranged so that light emitted from the first light emitter reaches an eye of the patient;
   c. a camera arranged to image the eye of the patient; and
   d. a controller that modulates a light emission from the first light emitter to create a light stimulus, that receives and analyses an electrical signal from the visual system of the patient and that provides an indication of visual system function based on that analysis,
   wherein the device is further modified so that one or more of the following conditions applies:
      (i) the device further comprises a second light emitter having a visible second emission spectrum that is distinct from the first emission spectrum, wherein:
         the optical assembly is arranged so that light emitted from the second light emitter reaches an eye of the patient,
         the controller measures the eye's pupil area using images from the camera and adjusts the luminance of light stimulus as a function of the eye's pupil area, and
         the controller modulates light emission from the first and second light emitters to create first and second flashes overlapping in time by at least 50% of the longer of the two flashes;
      (ii) the light stimulus comprises one or more flashes of light and the controller synchronizes the camera and the light stimulus so that the camera is only activated when there is no flash;
      (iii) the controller measures the eye's pupil area using images received from the camera and adjusts the luminance in the light stimulus through a non-linear, concave function of the eye's pupil area;
      (iv) the controller does not provide an indication of visual system function unless the eye's pupil has been identified;
      (v) the device further comprises a light detector adapted to measure light emitted from the first light emitter, wherein the controller does not provide an indication of visual system function if the signal from the light detector differs from a set of expected light detector signals that includes excessive external light;
      (vi) the device further comprises:
         an electrode array comprising three electrodes structurally adapted to be applied and removed from the skin as a single unit;
         an analog to digital converter that measures the electrical signal equal to the electric potential difference between a first electrode and a second electrode in the electrode array; and
         a common-mode attenuation circuit electrically connected to a third electrode in the electrode array, wherein the distance between the first and second electrode is greater than the distance between the first electrode and third electrode and the distance between the first and second electrode is greater than the distance between the second electrode and third electrode;
      (vii) the controller modulates a light emission from the first light emitter so as to deliver to the eye a periodic light stimulus that approximates a retinal illuminance that varies as one of a sinusoid, a square wave having a duty cycle between 30% and 70%, or a triangular wave; and
      (viii) the device further comprises an infrared light emitter having an emission spectrum that has at least 50% of its energy emitted at wavelengths longer than 710 nm, wherein:
         the optical assembly is further arranged so that light emitted from the infrared light emitter reaches the eye,
         the controller modulates a light emission from the infrared light emitter to create an infrared flash of light having a duration less than 40 ms, and
         the energy emitted by the first light emitter during the infrared flash of light is less than 50% of the energy emitted by infrared light emitter during the infrared flash of light.

2. The device of claim 1 wherein the device further comprises a second light emitter having a visible second emission spectrum that is distinct from the first emission spectrum, wherein:
   the optical assembly is arranged so that light emitted from the second light emitter reaches an eye of the patient,
   the controller measures the eye's pupil area using images from the camera and adjusts the luminance of light stimulus as a function of the eye's pupil area, and
   the controller modulates light emission from the first and second light emitters to create first and second flashes overlapping in time by at least 90% of the longer of the two flashes.

3. The device of claim 1, further comprising a third light emitter having a visible third emission spectrum that is distinct from the first emission spectrum and the second emission spectrum, wherein the optical assembly is further arranged so that light emitted from the third light emitter reaches the eye.

4. The device of claim 3, where the first light emitter is a green LED, the second light emitter is a red LED, and the third light emitter is a blue LED.

5. The device of claim 3 wherein the controller further modulates a light emission from the third light emitter to create a third flash of light, wherein the first flash, second flash, and third flash overlap in time by at least 50% of the longest of the three flashes.

6. The device of claim 5, where the overlap in time is at least 90% and the duration of the first flash, second flash, and third flash are all less than 6 ms.

7. The device of claim 1, wherein the light stimulus is periodic having a stimulus frequency within 0.1 Hz of 28.31, 28.72, or 32.55 Hz, or integer multiples thereof.

8. The device of claim 1, further comprising a light detector adapted to measure light emitted from the first light emitter, wherein the controller does not provide an indication of visual system function if a signal from the light detector differs from a set of expected light detector signals.

9. The device of claim 8, wherein the set of expected light detector signals that includes for external light not exceeding a threshold, wherein the threshold is a value between 1 $cd/m^2$ and 200 $cd/m^2$.

10. The device of claim 1, wherein:
    the light stimulus is periodic having a stimulus frequency greater than 7 Hz,
    the controller receives images from the camera at a frame rate, and the ratio of the stimulus frequency to the frame rate is within 1% of an integer or within 1% of the reciprocal of an integer.

11. The device of claim 1, wherein the controller does not provide the indication until after the eye's pupil has been identified.

12. The device of claim 1, wherein the controller modulates a light emission from the first light emitter so as to deliver to the eye a periodic light stimulus that approximates a retinal illuminance that varies as a sinusoid.

13. A device to provide an indication of visual system function of a patient comprising:
   a. a first light emitter having a visible first emission spectrum;
   b. a camera arranged to image an eye of the patient;
   c. an optical assembly arranged so that light emitted from the first light emitter reaches the eye; and
   d. a controller that modulates a light emission from the first light emitter to create a periodic light stimulus having a stimulus frequency, that receives and analyzes an electrical signal and that provides an indication of visual system function based on that analysis,
      wherein the controller receives images from the camera at a frame rate, measures the eye's pupil area using the received images, and adjusts the luminance of the light stimulus as a function of the eye's pupil area, and,
      wherein the controller controls the camera so that camera images are not taken when the periodic light stimulus is at its brightest.

14. A method for providing an indication of visual system function of a patient comprising:
   illuminating an eye of the patient with a light stimulus comprising a first flash of visible light having a duration of less than 21 ms and having a first emission spectrum;
   measuring the eye's pupil area and adjusting the energy in the first flash as a function of the eye's pupil area; and
   receiving and analyzing an electrical signal from the patient and providing an indication of visual system function based on that analysis;
   wherein the method further comprises at least one of the following steps:
   (i) illuminating the eye of the patient with a second flash of visible light having a duration of less than 21 ms and having a second emission spectrum distinct from the first emission spectrum and wherein the first flash and second flash overlap in time by at least 50% of the longer of the two flashes;
   (ii) adjusting the luminance in the light stimulus through a non-linear, concave function of the eye's pupil area;
   (iii) not providing an indication of visual system function unless the eye's pupil has been identified;
   (iv) not providing an indication of visual system function if a signal from a light detector differs from a set of expected light detector signals that includes excessive external light;
   (v) placing an electrode array comprising three electrodes on the skin of the patient as a single unit, wherein the three electrodes include a first electrode, a second electrode and a third electrode, the first and second electrode are more distant from each other than any other pairing of the first, second, and third electrodes, and electrically connecting a common-mode attenuation circuit to the third electrode;
   (vi) modulating a light emission from the first light emitter so as to deliver to the eye a periodic light stimulus that approximates a retinal illuminance that varies as one of a sinusoid, a square wave having a duty cycle between 30% and 70%, or a triangular wave; and
   (viii) illuminating the eye of the patient with infrared flashes of light that have at least 50% of their energy emitted at wavelengths longer than 710 nm and an infrared flash frequency greater than 1 Hz, and wherein the energy in the light stimulus emitted during the infrared flashes is less than 50% of the infrared energy emitted during the infrared flashes.

15. The method of claim 14, comprising illuminating the eye of the patient with a second flash of visible having a duration of less than 21 ms and having a second emission spectrum distinct from the first emission spectrum and wherein the first and second flashes of visible light overlap in time by at least 90% of the longer of the two flashes of visible light.

16. The method of claim 14 wherein:
   the light stimulus comprises flashes of light having a flash frequency greater than 7 Hz;
   the measuring the eye's pupil area occurs at a frame rate frequency; and
   the ratio of the flash frequency to the frame rate frequency is within 1% of an integer or within 1% of the reciprocal of an integer.

17. The method of claim 14 wherein the light stimulus is periodic having a stimulus frequency within 0.1 Hz of 28.31, 28.72, or 32.55 Hz, or integer multiples thereof.

18. The method of claim 14 further comprising illuminating the eye with a third flash of visible light having a third emission distinct from the first emission spectrum and the second emission spectrum, wherein the first flash, the second flash, and the third flash overlap in time by at least 90% of the longer of the three flashes, and the duration of the first flash, second flash and third flash are all less than 6 ms.

19. The method of claim 14 comprising not providing an indication of visual system function if a signal from a light detector differs from a set of expected light detector signals that includes monitoring for external light exceeding a threshold, wherein the threshold is a value between 1 cd/m$^2$ and 200 cd/m$^2$.

20. The method of claim 14 comprising modulating a light emission from the first light emitter so as to deliver to the eye a periodic light stimulus that approximates a retinal illuminance that varies as a sinusoid.

* * * * *